United States Patent
Holt et al.

Patent Number: 5,661,156
Date of Patent: Aug. 26, 1997

[54] RAPAMYCIN DERIVATIVES

[75] Inventors: Dennis Alan Holt, Stow, Mass.; Juan Ignacio Luengo, Audubon; Leonard Walter Rozamus, Jr., Chestersprings, both of Pa.

[73] Assignee: SmithKline Beecham Corporation, Philadelphia, Pa.

[21] Appl. No.: 373,182

[22] PCT Filed: Jul. 16, 1993

[86] PCT No.: PCT/US93/06680

§ 371 Date: Mar. 6, 1995

§ 102(e) Date: Mar. 6, 1995

[87] PCT Pub. No.: WO94/02137

PCT Pub. Date: Feb. 3, 1994

Related U.S. Application Data

[63] Continuation of Ser. No. 915,147, Jul. 17, 1992, abandoned.

[51] Int. Cl.$^6$ .................... A61K 31/395; C07D 267/00
[52] U.S. Cl. ............................ 514/291; 540/456
[58] Field of Search ........................ 540/456; 514/291

[56] References Cited

U.S. PATENT DOCUMENTS

| | | | |
|---|---|---|---|
| 5,023,263 | 6/1991 | Von Burg | 514/291 |
| 5,130,307 | 7/1992 | Failli et al. | 514/321 |
| 5,284,877 | 2/1994 | Organ et al. | 540/456 |

*Primary Examiner*—Robert T. Bond
*Attorney, Agent, or Firm*—Yuriy P. Stercho; Stephen A. Venetianer; Edward T. Lentz

[57] ABSTRACT

Rapamycin derivatives of formula

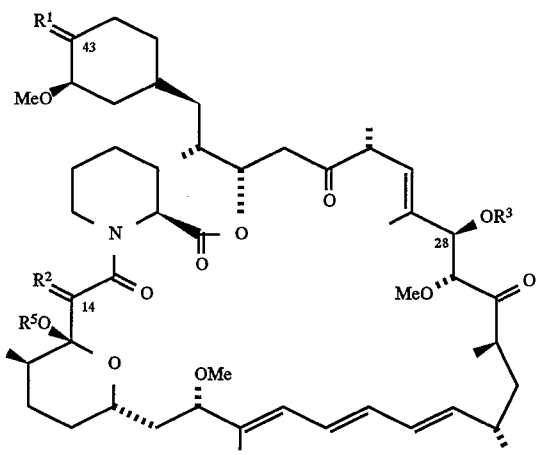

pharmaceutical compositions comprising such rapamycin derivatives and pharmaceutically acceptable carriers or diluents; and methods of using such derivatives to inhibit pathogenic fungal growth, cause therapeutically desirable immunosuppression, or treat carcinogenic tumors are disclosed.

17 Claims, No Drawings

RAPAMYCIN DERIVATIVES

This application is a 35 USC 371 of PCT/US 63/06680, filed 16 Jul. 1993, which is a continuing application of Ser. No. 07/913,142, filed 12, Jul. 1992, now abandoned.

BACKGROUND OF THE INVENTION

This invention relates to rapamycin derivatives, pharmaceutical compositions comprising such derivatives, and methods of treatment of pathogenic fungi, methods of inducing immunosuppression and methods of treating carcinogenic tumors utilizing such rapamycin derivatives.

Rapamycin is a naturally occurring macrocyclic triene antibiotic which can be produced by culturing an organism in an aqueous nutrient medium. Its structure may be illustrated as follows:

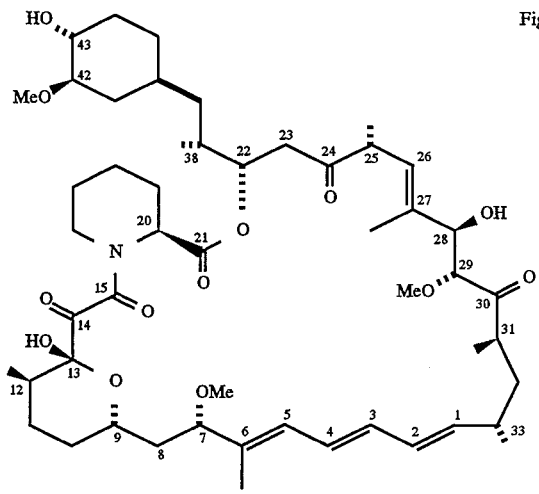

Figure I

At least one rapamycin-producing strain of *Streptomyces hygroscopius* was deposited with the Northern Utilization and Research Division, Agricultural Research Service, U.S. Department of Agriculture, Peoria, Ill., U.S.A. under accession number NRRL 5491. Rapamycin, and methods for its preparation by culturing NRRL 5491 are disclosed by U.S. Pat. No. 3,929,992, issued Dec. 30, 1975, the entire disclosure of which is hereby incorporated by reference.

SUMMARY OF THE INVENTION

This invention relates to novel rapamycin derivatives of the formula:

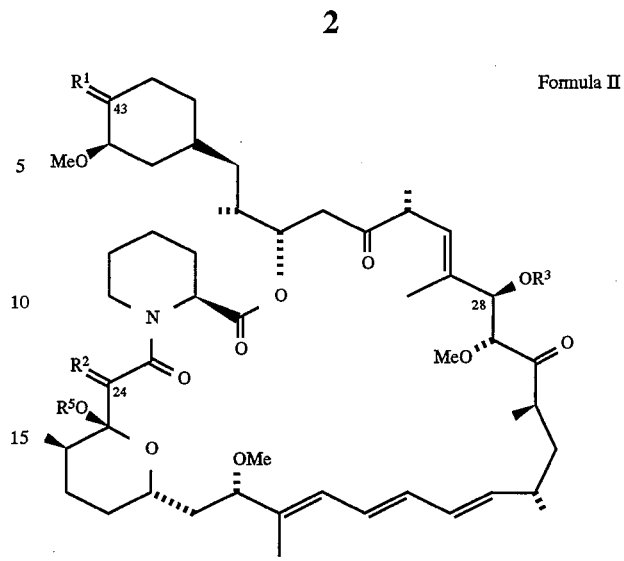

Formula II wherein:

$R^1$ is selected from the group consisting of =O, (—$OR^6$, H) and (H,H);

$R^2$ is selected from the group consisting of =O or (H,H), provided that $R^2$ is (H,H) when $R^1$ is (—$OR^6$,H) or =O;

$R^3$ and $R^6$ are independently selected from the group consisting of —H, —C(=O)$R^7$, —C(=O)O$R^7$, —C(=O)NH$R^7$, and —C(=S)O$R^7$;

$R^5$ is selected from the group consisting of —H and $C_1$–$C_4$ alkyl; and $R^7$ is selected from the group consisting of C1–C10 alkyl, $C^3$–$C^6$ cycloalkyl, aryl groups, and heterocyclic groups;

provided that, when $R^1$ is =O, then at least one of the following: (a) $R^2$ is other than =O, (b) $R^3$ is other than H, and (c) $R^5$ is other than H.

and all pharmaceutically acceptable salts, hydrates or solvates thereof.

This invention also relates to a pharmaceutical composition comprising an effective amount of one or more compounds of Formula II and a pharmaceutically acceptable carrier or diluent.

This invention also relates to a method of inhibiting the growth of pathogenic fungi in a human or other animal in need thereof which comprises administering an effective, non-toxic amount of one or more compounds of Formula II to such human or other animal.

This invention also relates to a method of inducing immunosuppression in a human or other animal in need thereof which comprises administering an effective, non-toxic amount of one or more compounds of Formula II to such human or other animal.

In addition, this invention relates to a method of treating carcinogenic tumors in a human or other animal comprising administering an effective, non-toxic amount of one or more compounds of Formula II to such human or other animal.

Still further, this invention relates to compounds of Formula III which are useful as intermediates for preparing compounds of Formula II:

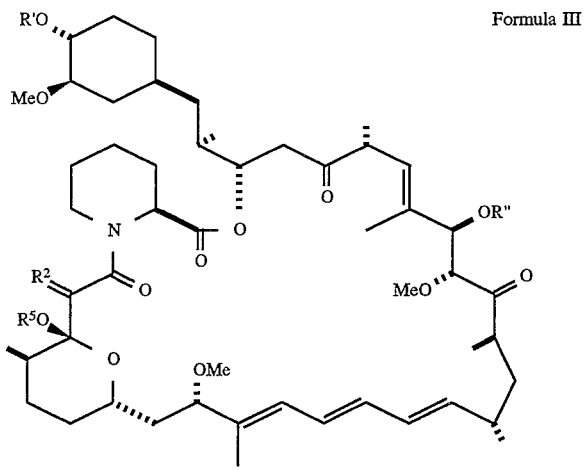

Formula III where R' is —(S)COPh, where Ph is phenyl;

R" is selected from the group consisting of H and —(S)COPh, and where $R^2$ and $R^5$ are as defined above.

Still further, this invention relates to a method of preparing novel compounds of Formula II from intermediates of Formula III.

DETAILED DESCRIPTION OF THE INVENTION

When any substituent or variable (e.g., aryl, alkoxyl, $R^1$, $R^2$, $R^3$, $R^5$, $R^6$, etc.) occurs more than one time in the formula of any of the compounds of Formula II, such variable or substituent definition on each occurrence is independent of its definition at every other occurrence, unless otherwise indicated. Combinations of substituents and/or variables are in a constituent of the compounds of the invention are permissible only if such combinations result in a stable compound.

The parenthetical nomenclature used in the definition of substituents such as $R^1$ (e.g., (H, $OR^6$) is intended to reflect the substituents on both valences of the relevant atom. The invention is not limited to particular isomers and the order of moieties in the parentheses does not suggest a particular configuration.

As used herein, except where otherwise noted, the term "alkyl" is intended to include both branched- and straight-chain saturated and unsaturated aliphatic hydrocarbon groups. Preferred alkyl groups have one to six carbon atoms, unless otherwise noted. Such alkyl group may be optionally substituted by one or more members independently selected from the group consisting of aryl, hydroxyl, $C_1$–$C_6$ alkoxyl, acyloxy, amino, N-acylamino, ketone, halogen, cyano and carboxyl. The term "alkyl" also includes the above-mentioned groups in which a heteroatom selected from oxygen, nitrogen and sulfur is substituted for one or more carbon atoms in the alkyl moiety.

As used herein, the term "aryl" is intended to include cyclic, heterocyclic, polycyclic and heteropolycyclic unsaturated $C_4$ to $C_{14}$ moieties, especially phenyl or naphthyl. Such aryl may be optionally substituted by one to five members independently selected from the group consisting of $C_1$–$C_6$ alkyl, aryl, hydroxyl, protected hydroxyl, $C_1$–$C_6$ alkoxyl, acyloxy, amino, N-acylamino, —S(O)n alkyl, nitro, cyano, carboxyl and halogen.

As used herein, the term "alkoxyl" represents an alkyl group as herein defined of the indicated number of carbon atoms attached through an oxygen bridge.

As used herein, the term "acyloxy" is intended to represent the groups —OC(O)-(alkyl) and —OC(O)-(aryl).

As used herein, the term "amino" is intended to represent the groups —$NH_2$, —N(alkyl)$_2$, —NH(alkyl), —N(aryl)$_2$, and —NH(aryl).

As used herein, the term "N-acylamino" is intended to represent the groups —NHC(O)-(alkyl) and —NHC(O)-(aryl).

As used herein, the term "ketone" is intended to mean the moiety —C(O)—.

As used herein, the term "halogen is intended to include fluoro, chloro, bromo and iodo.

As used herein, the term "cycloalkyl" is intended to include saturated and unsaturated hydrocarbon aliphatic ring groups having the specified number of carbon atoms. Such cycloalkyl may be optionally substituted by one or more members independently selected from the group consisting of aryl, hydroxyl, $C_1$–$C_6$ alkoxyl, acyloxy, amino, N-acylamino, ketone, and halogen.

As used herein, the term "heterocycle" is intended to include a stable 5- to 7-membered mono- or bicyclic or stable 7- to 10-membered bicyclic heterocyclic ring which is either saturated or unsaturated, and which consists of carbon atoms and from one to three heteroatoms independently selected from the group consisting of N, O and S, and wherein the nitrogen and sulfur heteroatoms may optionally be oxidized, and the nitrogen heteroatom may optionally be quarternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include but are not limited to piperidyl, piperidinyl, piperazinyl, pyrimidinyl, pyridazinyl, oxazolyl, furyl, and thienyl. The heterocycle may be optionally substituted in a manner such that carbon atoms attached to a heteroatom are not directly substituted by a heteroatom, by from one to four members independently selected from the group consisting of $C_1$–$C_6$ alkyl, aryl, hydroxyl, $C_1$–$C_6$ alkoxyl, acyloxy, amino, N-acylamino, nitro and halogen.

Preferred compounds of the invention include the following compounds wherein, together or independently:

1. $R^1$ is selected from the group consisting of (H,H), (H,OH) and =O;
2. $R^2$ is =O;
3. $R^3$ is H; and
4. $R^5$ is H.

Specifically preferred compounds are the following:

1. $R^1$ is (H,H), $R^2$ is =O, $R^3$ is —H and $R^5$ is —H.
2. $R^1$ is (H,OH), $R^2$ is (H,H), $R^3$ is —H and $R^5$ is —H.
3. $R^1$ is (H,H), $R^2$ is (H,H), $R^3$ is —H and $R^5$ is —H.
4. $R^1$ is =O, $R^2$ is (H,H), $R^3$ is —H and $R^5$ is H.
5. $R^1$ is (H,H), $R^2$ is (H,H), $R^3$ is —C(—O)$R^6$) and $R^5$ is —H.
6. $R^1$ is (H,H), $R^2$ is =O, $R^3$ is —C(=O)$R^6$, and $R^5$ is H.
7. $R^1$ is (H, OC(O)$OR^7$), $R^2$ is (H,H), $R^3$ is —H, and $R^5$ is —H.
8. $R^1$ is (H,OH), $R^2$ is (H,H), $R^3$ is —H, and $R^5$ is $C_1$–$C_4$ alkyl.

The compounds of this invention can exist in free form or, where appropriate, in salt form. Pharmaceutically acceptable salts and their preparation are well-known to those of skill in the art. The pharmaceutically acceptable salts of the compounds of this invention include the conventional nontoxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

The compounds of this invention may be prepared from rapamycin by methods disclosed below or conventional variations thereof using reagents that are either described in the literature or are commercially available.

Certain compounds of the invention may be prepared from novel phenylthionocarbonate intermediates of Formula III. The preparation of these intermediates, and their conversion to compounds of the invention is illustrated in Scheme A. As shown in Scheme A, rapamycin (although a derivatized rapamycin could also be utilized) is contacted with phenylchlorothionoformate in the presence of a base such as dimethylaminopyridine (DMAP) to prepare rapamycin derivatized at C-28 and/or C-43 atoms. These intermediates (Formula III) may be converted to compounds of this invention by reaction with a free-radical-based reductant such as trialkyltin hydride or tris(trimethylsilyl)silane and a radical initiator such as azobisisobutyronitrile (AIBN), benzoyl peroxide or triethylborane.

Scheme A

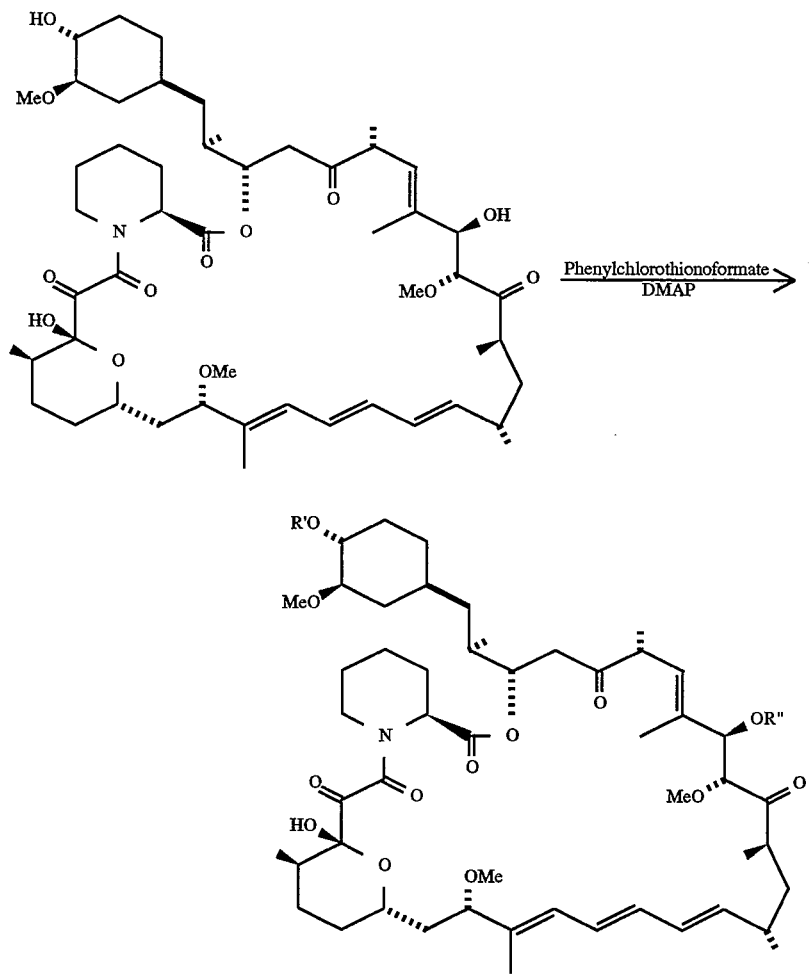

1. R' = R" = PhOC(S)- (29%)
2. R' = PhOC(S)-, R" = H (28%)
3. R' = H, R" = PhOC(S)- (22%)

-continued
Scheme A
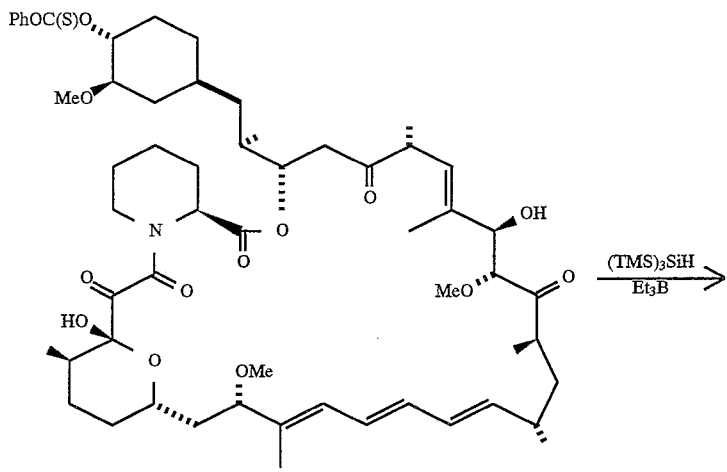
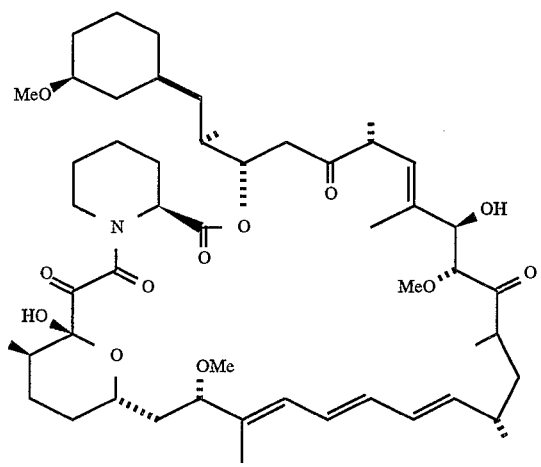
Compounds of the invention with an oxy (=O) moiety at C-43 may be prepared as illustrated in Scheme B. Scheme B illustrates the preparation of 43-dehydrorapamycin, which is useful as an intermediate for preparing other compounds of the invention.
Scheme B
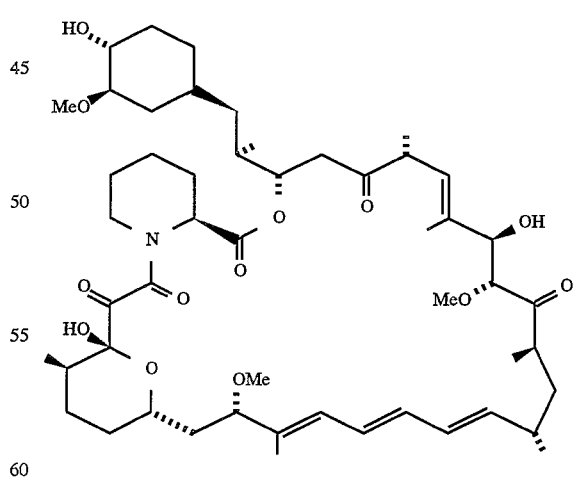

-continued
Scheme B

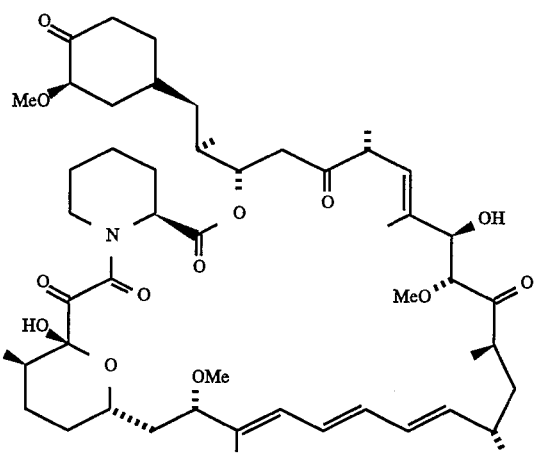

Compounds of the invention which are derivatized at C-28 may be prepared by contacting a compound where $R^5$ is H with an appropriate acid chloride (e.g., $R^7C(O)Cl$, $R^7OC(O)Cl$, $R^7NHC(O)Cl$ or $R^7OC(S)Cl$) in the presence of a base such as dimethylaminopyridine.

The Examples provided below in this specification provide a variety of synthetic methods for preparing compounds of this invention.

This invention also relates to pharmaceutical compositions comprising a pharmaceutically acceptable carrier or diluent and an effective amount of one or more compounds of Formula II.

A compound of Formula II is administered in conventional dosage form prepared by combining a therapeutically effective amount of the compound ("active ingredient") with standard pharmaceutical carrier or diluents according to conventional procedures. These procedures may involve mixing, granulating and compressing or dissolving the ingredients as appropriate to the desired preparation.

The pharmaceutical carrier employed may be, for example, either a solid or liquid. Exemplary of solid carrier are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax, ethylcellulose, hydroxypropylmethylcellulose, methylmethacrylate and the like.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of a compounds of the invention is dissolved in an aqueous solution of an organic or inorganic acid, such as a 0.3M solution of succinic acid, or, preferably, citric acid. Alternatively, acidic derivatives can be dissolved in suitable basic solutions. If a soluble salt form is not available, the compounds of the invention is dissolved in a suitable cosolvent or combinations thereof. Examples of such suitable cosolvents include, but are not limited to, alcohol, propylene glycol, polyethylene glycol 300, polysorbate 80, glycerin and the like in concentrations ranging from 0–60% of the total volume.

Tests indicate that the compounds of this invention are useful in prophylactically or therapeutically inhibiting the growth of pathogenic fungi in a human or other animal in need thereof. The invention, therefore, includes methods of inhibiting the growth of pathogenic fungi in a human or other animal in need thereof which comprises administering to such human or animal an effective, non-toxic amount of a compound of Formula II.

By the term "pathogenic fungi" is meant fungi capable of producing disease in a human or other animal. Examples of pathogenic fungi include, but are not limited to *Candida albicans* and other candida species, *Microsporum gypseum*, *Trichophyton mentagrophytes*, Asperqillus sp. and Sporotrichum sp. The ability of the compounds of this invention to inhibit the growth of pathogenic fungi may be demonstrated or predicted by standard tests known and used for this purpose, for example, the yeast assay described hereinbelow.

One skilled in the art would be able, by routine experimentation, to determine what an effective, non-toxic amount of compound would be for the purpose of inhibiting pathogenic fungi growth. Generally, however, an effective dosage will be in the range of about 0.05 to 100 milligrams per kilogram body weight per day.

Tests indicate that the compounds of this invention are also useful for inducing immunosuppression, i.e., inducing a suppression of a human's or animal's immune system. This invention therefore relates to a method of prophylactically or therapeutically inducing immunosuppression in a human or other animal in need thereof which comprises administering an effective, non-toxic amount of such a compound of this invention to such human or other animal.

The ability of the compounds of this invention to induce immunosuppression may be demonstrated in standard tests used for this purpose, for example, a mixed lymphocyte reaction test or a test measuring inhibition of T-cell proliferation measured by thimidine uptake.

The fact that the compounds of this invention have utility in inducing immunosuppression means that they are useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically mediated diseases (e.g., rheumatoid arthritis, lupus erythematosus, systemic lupus erythematosus, *Hashimotos thyroidiris*, multiple sclerosis, myasthenia gravis, type 1 diabetes, uveitis, nephrotic syndrome, psoriasis, atopical dermatitis, contact dermatitis and further eczematous dermatitides, seborrheic dermatitis, *Lichen planus*, Pemplugus, bullous Pemphigold, *Epidermolysis bullosa*, uritcaris, angiodemas, vasculitides, erythemas, cutaneous eosinophilias, *Alopecia areata*, etc.); the treatment of reversible obstructive airways disease, intestinal inflammations and allergies (e.g., Coeliac disease, proctitis, eosinophilia gastroenteritis, mastocytosis, Chrohn's disease and ulcerative colitis) and food related allergies (e.g., migrane, rhinitis, and eczema).

One skilled in the art would be able, by routine experimentation, to determine what an effective, non-toxic amount of compound would be for the purpose of inducing immunosuppression. Generally, however, an effective dosage will be in the range of about 0.05 to 100 milligrams per kilogram body weight per day.

The compounds of this invention should also be useful for treating carcinogenic tumors in a mammal. More specifically, the compounds should be useful for reducing tumor size, inhibiting tumor growth and/or prolonging the survival time of tumor-bearing animals. Accordingly, this invention also relates to a method of treating carcinogenic tumors in a human or other animal comprising administering to such human or animal an effective, non-toxic amount of a compound of Formula II. One skilled in the art would be able, by routine experimentation, to determine what an effective, non-toxic amount of compound would be for the purpose of treating carcinogenic tumors. Generally, however, an effective dosage is expected to be in the range of about 0.05 to 100 milligrams per kilogram body weight per day.

The compounds of the invention may be administered to a human or other animal in accordance with the aforementioned methods of treatment in an amount sufficient to produce such effect to a therapeutic or prophylactic degree. Such compound of the invention can be administered to such human or other animal in a conventional dosage form prepared by Combining the compound of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the compound of the invention may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred.

The daily parenteral and oral dosage regimens for employing compounds of the invention to prophylactically or therapeutically inhibit the growth of pathogenic fungi, to prophyliatically or therapeutically induce immunosuppression, or to therapeutically treat carcinogenic tumors will generally be in the range of about 0.05 to 100, but preferably about 0.5 to 10, milligrams per kilogram body weight per day.

The compounds of the invention may also be administered by inhalation. By "inhalation" is meant intranasal and oral inhalation administration. Appropriate dosage forms for such. administration, such as an aerosol formulation or a metered dose inhaler, may be prepared by conventional techniques. The preferred dosage amount of a compound of the invention to be employed is generally within the range of about 10 to 100 milligrams.

The compounds of the invention may also be administered topically. By topical administration is meant non-systemic administration and includes the application of a compounds of the invention externally to the epidermis, to the buccal cavity and instillation of such a compound into the ear, eye and nose, and where the compound does not significantly enter the blood stream. By systemic administration is meant oral, intravenous, intraperitoneal and intramuscular administration. The amount of a compound of the invention (hereinafter referred to as the active ingredient) required for therapeutic or prophylactic effect on pathogenic fungi growth inhibition or immunosuppression induction upon topical administration will, of course, vary with the compound chosen, the nature and severity of the condition being treated and the animal undergoing treatment, and is ultimately at the discretion of the physician. A suitable topical dose of a compound of the invention will generally be within the range of about 1 to 100 milligrams per kilogram body weight daily.

While it is possible for an active ingredient to be administered alone as the raw chemical, it is preferable to present it as a pharmaceutical formulation. The active ingredient may comprise, for topical administration, from 0.001% to 10% w/w, e.g., from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefore and optionally any other therapeutic ingredient(s). The carrier(s) must be "acceptable" in the sense of being compatible with the other ingredients of the formulation and no deleterious to the recipient thereof.

Formulations suitable for topical administration include liquid or semi-liquid preparations suitable for penetration through the skin to the site of where treatment is required such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active such as sorbitan esters or polyoxyethylene derivatives thereof. Suspending agents such as natural gums, cellulose derivatives or in organic materials such as silicaceous silicas, and other ingredients such as lanolin, may also be included.

It will be recognized by one of skill in the art that the optimal quantity and spacing of individual dosages of the compound of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the compound of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

I. COMPOSITION EXAMPLES

EXAMPLE A—CAPSULE COMPOSITION

A pharmaceutical composition of this invention in the form of a capsule is prepared by filling a standard two-piece hard gelatin capsule with 50 mg of a compound of the invention, in powdered form, 100 mg of lactose, 32 mg of talc and 8 mg of magnesium stearate.

EXAMPLE B—INJECTABLE PARENTERAL COMPOSITION

A pharmaceutical composition of this invention in a form suitable for administration by injection is prepared by stirring 1.5% by weight of a compound of the invention in 10% by volume propylene glycol and water. The solution is sterilized by filtration.

EXAMPLE C—OINTMENT COMPOSITION

Compound of the invention 1.0 g
White soft paraffin to 100.0 g

The compound of the invention is dispersed in a small volume of the vehicle and gradually incorporated into the bulk of the vehicle to produce a smooth, homogeneous product. Collapsible metal tubes are then filled with the dispersion.

EXAMPLE D—TOPICAL CREAM COMPOSITION

Compound of the invention 1.0 g
Polawax GP 200 20.0 g
Lanolin Anhydrous 2.0 g
White Beeswax 2.5 g
Methyl hydroxybenzoate 0.1 g
Distilled Water to 100.0 g The polawax, beeswax and lanolin are heated together at 60 C. A solution of methyl hydroxybenzoate is added and homogenization is achieved using high speed stirring. The temperature is then allowed to fall to 50 C. The compound of the invention is then added and dispersed throughout, and the composition is allowed to cool with slow speed stirring.

EXAMPLE E—TOPICAL LOTION COMPOSITION

Compound of the invention 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml The methyl hydroxybenzoate and glycerin are dissolved in 70 ml of the water at 75 The sorbitan monolaurate, polysorbate 20 and cetostearyl alcohol are melted together at 75 C. and added to the aqueous solution. The resulting emulsion is homogenized, allowed to cool with continuous stirring and the compound of the invention is added as a suspension in the remaining water. The whole suspension is stirred until homogenized.

EXAMPLE F—EYE DROP COMPOSITION

Compound of the invention 0.5 g
Methyl Hydroxybenzoate 0.01 g
Propyl Hydroxybenzoate 0.04 g
Purified water B.P. to 100.00 ml (B.P.=British Pharmacopia)

The methyl and propyl hydroxybenzoates are dissolved in 70 ml purified water at 75 C. and the resulting solution is allowed to cool. The compound of the invention is then added, and the solution is sterilized by filtration through a membrane filter (0.22 mu m pore size) and packed aseptically into suitable sterile containers.

EXAMPLE G—COMPOSITION FOR ADMINISTRATION BY INHALATION

For an aerosol container with a capacity of 15–20 ml: Mix 10 mg of a compound of the invention with 0.2–0.2% of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration

EXAMPLE H—COMPOSITION FOR ADMINISTRATION BY INHALATION

For an aerosol container with a capacity of 15–20 ml: Dissolve 10 mg of a compound of the invention in ethanol (6–8 ml), add 0.1–0.2% of a lubricating agent, such as polysorbate 85 or oleic acid; and disperse such in a propellant, such as freon, preferably a combination of (1.2 dichlorotetrafluoroethane) and difluorochloromethane, and put into an appropriate aerosol container adapted for either intranasal or oral inhalation administration.

II. SYNTHETIC EXAMPLES

In the following Examples, rapamycin was obtained via fermentation, and all other starting materials and chemical reagents were obtained from commercial suppliers unless otherwise indicated.

Example 1

43-Deshydroxyrapamycin ($R^1$ is (H,H), $R^2$ is =O, $R^3$ is H and $R^5$ is H)

A. Rapamycin Phenylthionocarbonates

Rapamycin (80.5 mg, 88.1, mol) was dissolved in 1.5 mL of dry dichloromethane in an ice bath and under an argon atmosphere. Dimethylaminopyridine (80.0 mg, 0.655 mmol) and phenylchlorothionoformate (40.0 µL, 0.289 mmol) were then added. The resulting yellow-orange solution was allowed to stir for 4 hours (h), after which time analysis by thin layer chromatography (silica gel, 35% ethyl acetate/ petroleum ether) indicated the presence of three distinct products in addition to the presence of a minor amount of rapamycin. The reaction mixture was then diluted with 1.0 mL of dichloromethane, and this mixture was added directly to a flash chromatography column containing silica gel. Elution with 25% ethyl acetate/hexane yielded the 28,43-bis-thionocarbonate rapamycin derivative (28 mg, Rf=0.82) and the 43-thionocarbonate rapamycin derivative (18.5 mg, Rf=0.58). Continued elution with 60% ethyl acetate/hexane yielded the 28-thionocarbonate rapamycin derivative (18.5 mg, Rf=0.19) and residual rapamycin (6 mg, Rf=0.07).

B. 43-Deshydroxyrapamycin

Triethylborane (15 μL, 1.0M hexane solution) was added to a stirring solution of rapamycin-43-phenylthionocarbonate (10 mg, 9.5 mol) (prepared as described in Example 1A) in 0.2 ml of toluene at room temperature under an argon atmosphere. Tris(trimethylsilyl)silane (30 μL, 97 μmol) was added, and the resulting solution was allowed to stir for 10 minutes. An additional 10 μL of triethylborane solution was then injected, and the mixture was briefly exposed to air. After a total reaction time of 30 minutes, the solution was diluted with 0.5 mL of toluene, and added directly to a flash chromatography column. Elution with 25% ethyl acetate/hexane yielded 1.5 mg of 43-deshydroxyrapamycin as a white solid, melting point (m.p. 97°–100° C). The following NMR data was obtained for 43-deshydroxyrapamycin:

| Proton | Rapamycin (TMS) | 43-deshydroxyrapamycin (TMS) |
|---|---|---|
| Me(46)O | 3.41 (s) | 3.34 (s) |
| C(42)H | 2.93 (m) | 3.07 (m) |

Example 2

43-Dehydrorapamycin ($R^1$ is =O, $R^2$ is =O, $R^3$ is H, and $R^5$ is H)

Rapamycin (109.7 mg 0.12 μmol) was added to a reaction mixture containing tetrapropylammonium perruthenate (8.4 mg, 24 μmol), N-methylmorpholine oxide (42.2 mg, 0.36 μmol) and 4A molecular sieves (120 mg) in dichloromethane (1.2 mL) at 0° C. for 3 h. TLC (thin layer chromatography) analysis of the reaction (silica gel, elution was 20:80 hexane/ethyl acetate) showed some starting unreacted rapamycin. Thus, additional amounts of tetrapropylammonium perruthenate (8.4 mg, 24 μmol) and N-methylmorpholine oxide (42.2 mg, 0.36 μmol) were added, and stirring continued at 0° C. for 2 more hours. The crude mixture (a black suspension) was purified by silica gel flash chomatography (gradient elution was 40:60 to 20:80 hexane/ethyl acetate) to yield 55 mg (50%) of 43-dehydrorapamycin as a white powder (Rf's in silica gel, 20:80 hexane/ethyl acetate: 0.45 for 43-dehydrorapamycin and 0.30 for rapamycin). The following NMR data was obtained for 43-dehydrorapamycin:

| Proton | Rapamycin (TMS) | 43-dehydrorapamycin (TMS) |
|---|---|---|
| Me(46)O | 3.41 (s) | 3.36 (s) |
| C(42)H | 2.93 (m) | 3.80 (dd) |

Example 3

14-Deoxorapamycin ($R^1$ is (H,OH), $R^2$ is (H,H), $R^3$ is H and $R^5$ is H)

Hydrogen sulfide was bubbled through a stirring solution of rapamycin (100 mg, 0.109 mmol) in 5 mL of 1:1 methanol-pyridine for 1 h at room temperature. The yellow reaction mixture was then covered and allowed to stir overnight. Excess hydrogen sulfide was disperse by a steady stream of argon, after which the solvent was removed under reduced pressure. Flash chromatography (80% ethyl acetate/hexane) of the resulting residue yielded the title compound, i.e., 14-Deoxorapamycin, as a white solid, m.p. 106°–109° C. The following NMR data was obtained for 14-deoxorapamycin:

| Proton | Rapamycin (TMS) | 43-deshydroxyrapamycin (TMS) |
|---|---|---|
| C(14)H's | N/A | 2.42 (d,J = 15.3 Hz) |
| C(20)H | 5.29 | 2.71 (d,J = 15.3 Hz) |

Example 4

43-Deshydroxy-14-Deoxorapamycin ($R^1$ is (H,H), $R^2$ is (H,H), $R^3$ is H and $R^5$ is H)

43-Deshydroxyrapamycin (100 mg) is dissolved in 5 mL of a 1:1 mixture of methanol and pyridine. Hydrogen sulfide is passed through the resulting solution for 1 hour. The reaction mixture is then allowed to stand for 1 day. Excess hydrogen sulfide is dispersed by bubbling argon through the solution which is then concentrated. The title compound is isolated from the residue by column chromatography on silica gel using an ethyl acetate-hexane mixture as eluent.

Example 5

43-Dehydro-14-Desoxorapamycin ($R^1$ is =O, $R^2$ is (H,H), $R^3$ is H and $R^5$ is H)

43-Dehydrorapamycin (100 mg, Example 4) is dissolved in 5 ml of a 1:1 mixture of methanol and pyridine. Hydrogen sulfine is passed through the resulting solution for 1 hour. The reaction mixture is then allowed to stand for 1 day. Excess hydrogen sulfide is dispersed by bubbling argon. through the solution which is then concentrated. The title compound is isolated from the residue by column chromatography on silica gel using an ethyl acetate-hexane mixture as eluent.

Example 6

43-Deshydroxy-14-Dexoxo-28-Acyloxyrapamycin ($R^1$ is (H,H), $R^2$ is (H,H), $R^3$ is —C(O)$R^7$, and $R^5$ is H)

43-Deshydroxy-14-desoxorapamycin (80 mg, Example 5) is dissolved in 1.5 ml of dry dichloromethane in an ice bath and under an argon atmosphere. Dimethylaminopyridine (80 mg) and an alkyl acid chloride ($R^7$C(O)Cl, 3 mmol) are then added. The solution is allowed to stir for 4 to 12 hours, after which time the reaction mixture is diluted with 1.0 ml dichloromethane and added directly to a flash chromatography column containing silica gel. Elution with an ethyl acetate/hexane mixture yields the title compound.

Example 7

43-Deshydroxy-28-Acyloxyrapamycin ($R^1$ is (H,H), $R^2$ is =O, $R^3$ is C(O)$R^7$ and $R^5$ is H)

The title compound is obtained using the same procedure as described for 43-deshydroxy-14-desoxo-28-acyloxyrapamycin (Example 6) except that 43-deshydroxy-14-desoxorapamycin is replaced with 43-deshydroxyrapamycin.

Example 8

43-Acyl-14-Desoxorapamycin ($R^1$ is (H,OC(O)$R^7$), $R^2$ is (H,H), $R^3$ is H and $R^5$ is H)

14-Desoxorapamycin (80 mg, Example 3) is dissolved in 1.5 ml dry dichloromethane, in an ice bath under an argon atmosphere. Dimethylaminopyridine (80 mg) and an alkyl acid chloride ($R^7$C(O)Cl, 3 mmol) are then added. The solution is allowed to stir for 4 to 12 hours, after which time the reaction mixture is diluted with 1.0 ml dichloromethane and added directly to a flash chromatography column containing silica gel. Elution with an ethyl acetate/hexane mixture yields the title compound as well as the 28,43-bisacylated 14-desoxorapamycin derivative.

Example 9

13-Alkoxy-14-Desoxorapamycin ($R^1$ is (H,OH), $R^2$ is (H,H), $R^3$ is H and $R^5$ is alkyl)14-Desoxorapamycin (80 mg, Example 3) is dissolved in 2 ml of a C1–C4 alcohol (such as methanol, ethanol, propanol) along with a catalytic amount (2 mg) of camphorsulfonic acid. The reaction mixture is allowed to stir at room temperature for one day after which time the solution is concentrated and the title compound is isolated from the residue by column chromatography.

III. BIOLOGICAL EXAMPLES

Compounds of the invention were analyzed for antifungal and immunosuppressive activity using the following assays.

Assay for Antifungal Activity

Yeast organism (*Saccharomyces cerevisiae*) in logarithmic growth were plated on complete agar medium (YPD). Compounds dissolved in an appropriate aqueous or organic solvent were placed in wells punched in the agar. Plates were incubated for 48 hours and zones of inhibition were measured. All of the compounds of the invention tested in this assay exhibited antifungal activity.

Mitogenesis Assay for Immunosuppressive Activity

Spleen cells from BDF1 female mice were established in RPMI with 10% fetal calf serum at $5\times10^6$/mL. One hundred mL aliquots of this suspension ($5\times 10^5$ cells) were dispensed into 96-well round-bottomed microtiter plates (Linbro, Flow Laboratories). Concanavalin A (5 µg/ml)was added as the mitogenic stimulus, and the final volume in the microtiter wells was adjusted to 200 µL with RPMI. Cell cultures were incubated for 72 hours at 37° C. in a 5% $CO_2$ atmosphere and pulsed with 0.5 µCi $^3$H-thymidine (specific activity 2.00 Ci/mole) for the last 18 hours of the 72 hour culture. The cells were harvested on an automated multiple sample harvester and cell-associated radioactivity counted in a Beckman liquid scintillation counter. The results are expressed as the mean values derived from quadruplicate measurements. Cell viability was determined by trypan blue exclusion after 72 hours of incubation. Compounds to be tested were added to the microtiter plates at the appropriate dilutions prior to the addition of cells. All of the compounds of the invention tested in this assay exhibited immunosuppressive activity.

Results of these two assays, i.e., antifungal activity assay and the mitogenesis assay for immunosuppressive activity, for compounds of this invention are provided in Table 1.

TABLE 1

Compound Activities

| Compound | Yeast $IC_{12}$ (ng/mL) | Mitogenesis $IC_{50}$ (nM) |
|---|---|---|
| 43-Deshydroxy-Rapamcyin (Example 1) | 8 | 0.5 |
| 14-Desoxo-Rapamycin (Example 3) | 13 | 15 |
| 14-Desoxo-13-Methoxy-Rapamycin | 52 | 1000 |

While the above descriptions and Examples fully describe the invention and the preferred embodiments thereof, it is understood that the invention is not limited to the particular disclosed embodiments coming within the scope of the following claims.

What is claimed is:

1. A compound of the formula II:

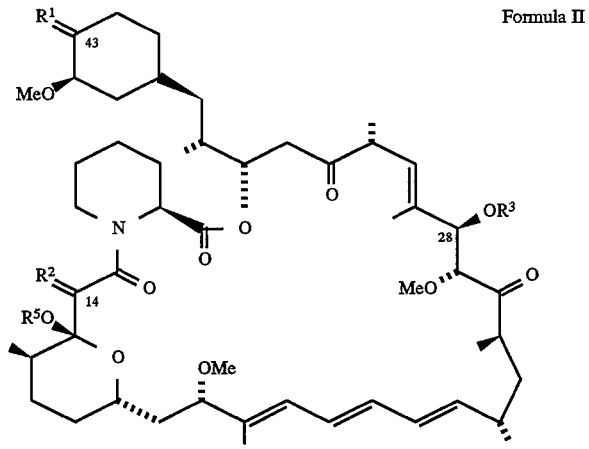

Formula II wherein:

$R^1$ is selected from the group consisting of =O, (—$OR^6$, H) and (H,H);

$R^2$ is selected from the group consisting of =O or (H,H), provided that $R^2$ is (H,H) When $R^1$ is (—$OR^6$,H) or =O;

$R^3$ and $R^6$ are independently selected from the group consisting of —H, —C(=O)$R^7$, —C(=O)O$R^7$, —C(=O)NH$R^7$, and —C(=S)O$R^7$;

$R^5$ is selected from the group consisting of —H and $C_1$–$C_4$ alkyl; and $R^7$ is selected from the group consisting of $C_1$–$C_{10}$ alkyl, $C_3$–$C_6$ cycloalkyl, phenyl and naphthyl optionally substituted by from one to five members selected from the group consisting of $C_1$–$C_6$ alkyl, phenyl, naphthyl, hydroxyl, $C_1$–$C_6$ alkoxyl, acyloxy, amino, N-acylamino, nitro, cyano and halogen and heterocyclic groups selected from the group consisting of piperidyl, piperidinyl, piperazinyl, pyrimidinyl, pyridazinyl, oxazolyl, furyl, and thienyl optionally substituted, in a manner such that carbon atoms attached to a heteroatom are not directly substituted by a heteroatom, by from one to four members selected from the group consisting of $C_1$-$C_6$ alkyl, phenyl, naphthyl, hydroxyl, $C_1$-$C_6$ alkoxyl, acyloxy, amino, N-acylamino, nitro, and halogen;

provided that, when $R^1$ is =O, then at least one of the following: (a) $R^2$ is other than =O, (b) $R^3$ is other than H, and (c) $R^5$ is other than H, and all pharmaceutically acceptable salts, hydrates or solvates thereof.

2. The compound of claim 1 where $R^1$ is selected from the group consisting of (H,H) and (H,OH).

3. The compound of claim 1 where $R^2$ is =O.

4. The compound of claim 1 where $R^3$ is H.

5. The compound of claim 1 where $R^5$ is H;

6. The compound of claim 1 wherein:

(a) $R^1$ is (H,H), $R^2$ is =O, $R^3$ is —H and $R^5$ is —H.

(b) $R^1$ is (H,OH), $R^2$ is (H,H), $R^3$ is —H and $R^5$ is —H;

(c) $R^1$ is (H,H), $R^2$ is (H,H), $R^3$ is —H and $R^5$ is —H;

(d) $R^1$ is =O, $R^2$ is (H,H), $R^3$ is —H and $R^5$ is H;

(e) $R^1$ is (H,H), $R^2$ is (H,H), $R^3$ is —C(O)$R^6$) and $R^5$ is —H;

(f) $R^1$ is (H,H), $R^2$ is =O, $R^3$ is —C(O)$R^6$, and $R^5$ is H;

(g) $R^1$ is (H, OC(O)O$R^6$), $R^2$ is (H,H), $R^3$ is —H and $R^5$ is —H; or (h) $R^1$ is (H,OH), $R^2$ is —H, $R^3$ is —H and $R^5$ is $C_1$-$C_4$ alkyl.

7. A pharmaceutical composition comprising a pharmaceutically acceptable carrier or diluent, and an effective therapeutic or prophylatic amount of one or more compounds of claim 1.

8. A pharmaceutical composition comprising a pharmaceutically acceptable carrier or diluent and an effective therapeutic or prophylactic amount of one or more compounds of claim 2.

9. A pharmaceutical composition comprising a pharmaceutically acceptable carrier or diluent and an effective therapeutic or prophylactic amount of one or more compounds of claim 3.

10. A pharmaceutical composition comprising a pharmaceutically acceptable carrier or diluent and an effective therapeutic or prophylactic amount of one or more compounds of claim 4.

11. A pharmaceutical composition comprising a pharmaceutically acceptable carrier or diluent and an effective therapeutic or prophylactic amount of a compound of claim 5.

12. A pharmaceutical composition comprising a pharmaceutically acceptable carrier or diluent and an effective therapeutic or prophylactic amount of a compound of claim 6.

13. A method of inhibiting the growth of pathogenic fungi in a human or other animal in need thereof which comprises administering to such human or other animal an effective, non-toxic amount of a compound of claim 1.

14. A method of inducing immunosuppression in a human or other animal in need thereof which comprises administering to such human or other animal an effective, non-toxic amount of a compound of claim 1.

15. A method of treating carcinogenic tumors in a human or other animal comprising administering to such human or animal an effective, non-toxic mount of a compound of claim 1.

16. The compound of the formula

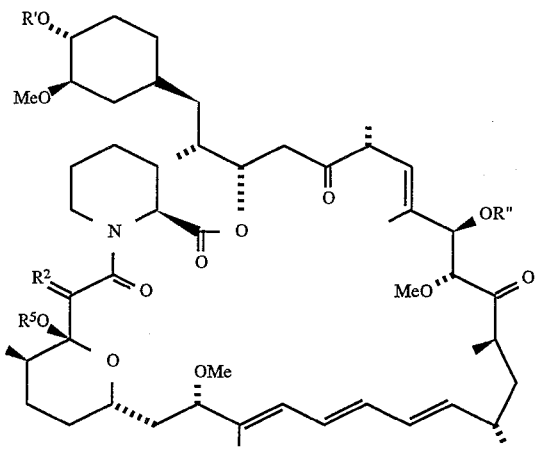

where R' is —(S)COPh where Ph is phenyl,

R" is from the group consisting of H and —(S)COPh, where Ph is phenyl, $R^2$ is selected from the group consisting of =O or (H,H); and $R^5$ is selected from the group consisting of —H and $C_1$-$C_4$ alkyl.

17. A method of preparing a compound of claim 1 comprising contacting a compound of the formula:

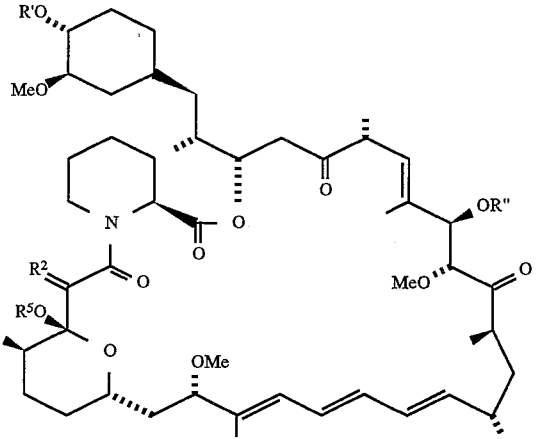

where R' is —(S)COPh where Ph is phenyl,

R" is from the group consisting of H and —(S)COPh, where Ph is phenyl, $R^2$ is selected from the group consisting of =O or (H,H); and $R^5$ is selected from the group consisting of —H and $C_1$-$C_4$ alkyl, with a free radical reductant selected from the group consisting of trialkyltin hydride and tris(trimethylsilyl)silane and a radical initiator selected from the group consisting of azobisisobutyronitrile, benzoyl peroxide and triethylborane.

* * * * *

Disclaimer 5,661,156 - Dennis Alan Holt, Stow, Mass.; Juan Ignacio Luengo, Audubon; Leonard Walter Rozamus, Jr., Chestersprings, both of Pa. RAPAMYCIN DERIVATIVES. Patent dated August 26, 1997. Disclaimer filed July 26, 1999, by SmithKline Beecham Corporation.

The term of this patent shall not extend beyond expiration date of Pat. No. 5,491,229.
*(Official Gazette, September 21, 1999)*